United States Patent [19]
Govignon

[11] 4,135,791
[45] *Jan. 23, 1979

[54] REDUCED GLARE SCANNER

[75] Inventor: Jacques P. Govignon, Malden, Mass.

[73] Assignee: Varian Associates, Inc., Palo Alto, Calif.

[*] Notice: The portion of the term of this patent subsequent to May 31, 1994, has been disclaimed.

[21] Appl. No.: 797,983

[22] Filed: May 18, 1977

Related U.S. Application Data

[63] Continuation of Ser. No. 528,740, Dec. 2, 1974, abandoned.

[51] Int. Cl.² .................................................. A61B 3/14
[52] U.S. Cl. ............................................ 351/7; 350/6; 350/3; 350/207; 350/285; 351/16; 351/39
[58] Field of Search ................... 351/6, 7, 13, 16, 39; 350/6, 96 B, 207, 266, 285

[56] References Cited

U.S. PATENT DOCUMENTS

| 3,259,041 | 7/1966 | Okajima ............................ 351/7 X |
| 3,536,383 | 10/1970 | Cornsweet et al. ...................... 351/6 |
| 4,026,638 | 5/1977 | Govignon .............................. 351/7 |

*Primary Examiner*—Paul A. Sacher
*Attorney, Agent, or Firm*—Thomas C. Stover, Jr.

[57] ABSTRACT

Method and apparatus for reduced glare observation of the eye fundus through optical lenses is accomplished by synchronized scanning illumination and observation of successive portions of the fundus. The scanning is conducted in rapid cycles to obtain continuous observation of the fundus and to provide for reduced glare photographs thereof.

31 Claims, 26 Drawing Figures

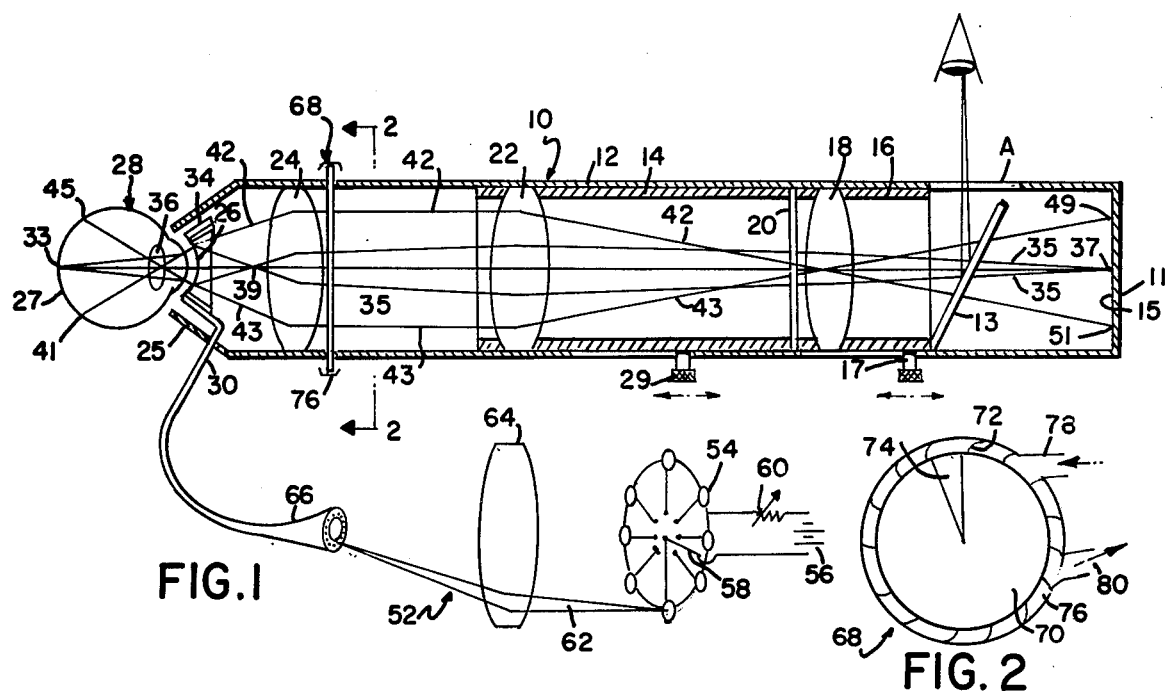
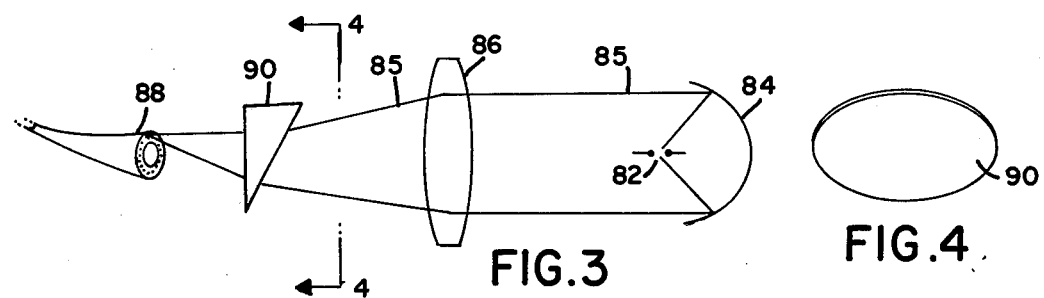
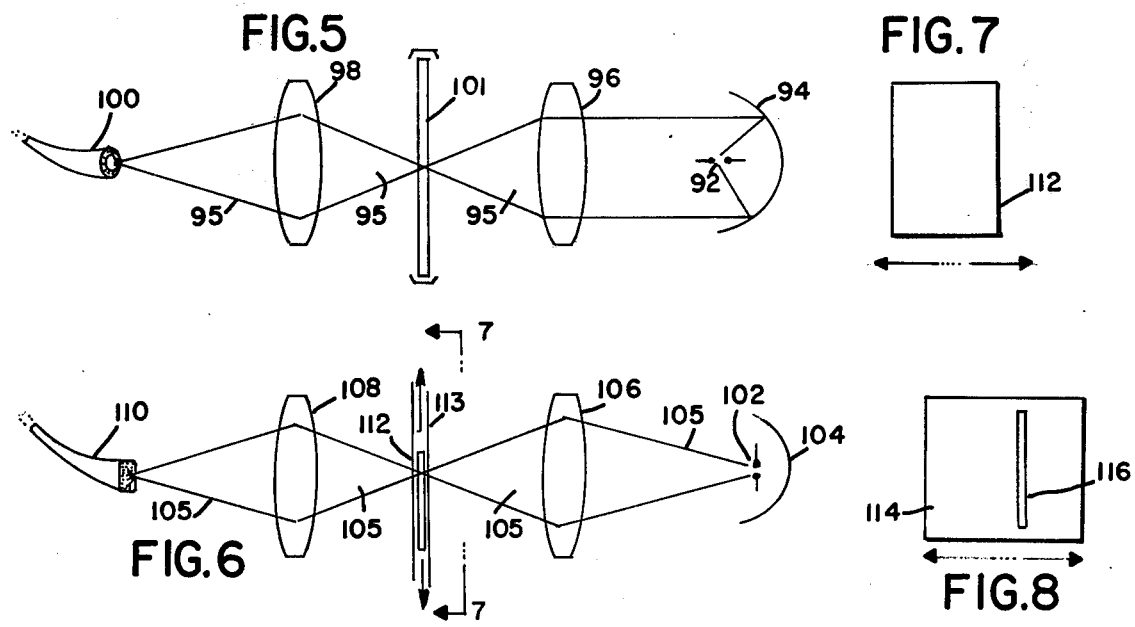

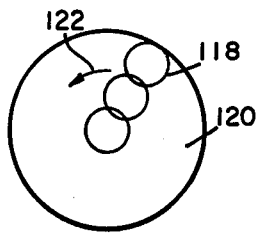
FIG.9
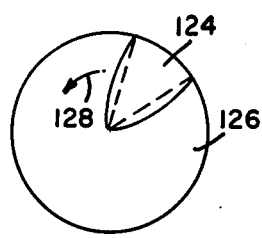
FIG.10
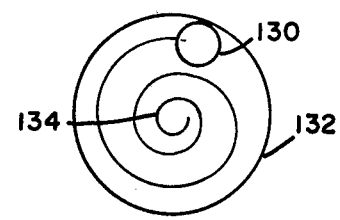
FIG.11
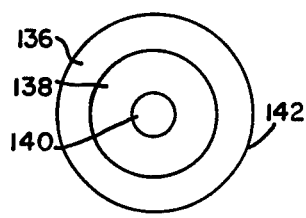
FIG.12
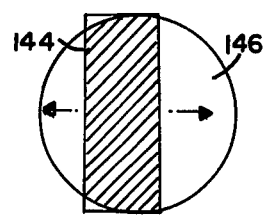
FIG.13
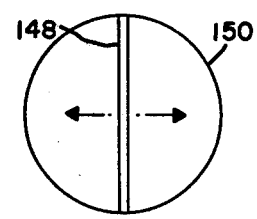
FIG.14
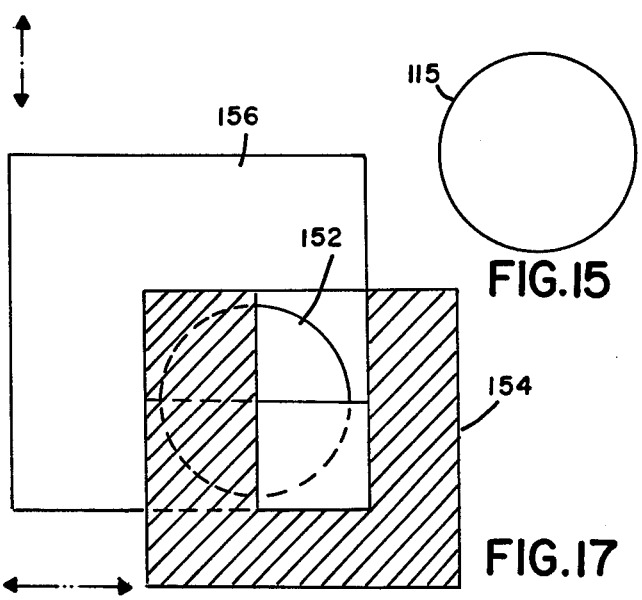
FIG.15
FIG.16
FIG.17
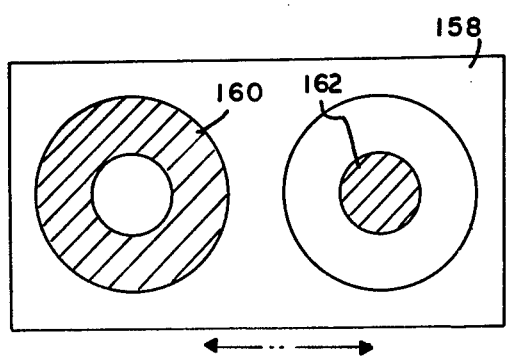
FIG.18

REDUCED GLARE SCANNER

This is a continuation of application Ser. No. 528,740, filed Dec. 2, 1974 and now abandoned.

FIELD OF THE INVENTION

This invention relates to a method and apparatus for reduced glare illumination and observation of an article through transparent, reflective and diffusive media, particularly such illumination and observation utilizing a scanning means.

THE PRIOR ART

Illumination of objects through transparent reflective and diffusive media, e.g. lenses or water for observation and photography thereof is widely practiced with attempts being made to reduce light reflection and diffusion in the media which cause glare and haze interference. For example, in the illumination of the eye interior where the light is reflected back out from the eye through the lens therein, the pupil, and through a lens system to an image receiving means, i.e. a camera or observer, light reflected and diffused in the lens system results in glare interference which obscures the image received. To reduce such glare a diaphragm is placed in the lens system and the aperture thereof adjusted in alignment with the eye pupil, so as to screen out much of the glare or haze from the image observed or photographed. Further, glare reduction is obtained by illuminating the fundus outside of the lens observation system; see, for example, my copending U.S. Patent application Ser. No. 455,975, now U.S. Pat. No. 4,023,189, entitled "Wide Angle Fundus Illumination and Photography Apparatus." However, even with the above measures, appreciable glare or haze still is transmitted with the resultant image.

Accordingly, there is a need and market for a method and apparatus which further reduces the glare and haze from the resultant image of such articles particularly in the observation and photography thereof.

There has now been discovered a method and apparatus for observing and photographing objects through transparent, reflective and diffusive media, by sequentially illuminating the object while employing in the image receiving system, a glare shield or diaphragm with a moveable aperture, which sequentially scans the so-illuminated object synchronously with the illuminating device by projecting a moving glare-reducing entrance pupil thereon while screening out reflected glare to obtain a reduced glare image thereof.

SUMMARY

Broadly the present invention provides a method and apparatus for reduced glare observation of an article through transparent, reflective and diffusive media comprising, an image receiving means; illumination means which beams light to said article, said media being mounted proximate said article, said light being reflected from said article through said media to said image receiving means; light directing means to direct said light to rapidly and repeatedly illuminate successive portions of said article; an observation diaphragm positioned between at least a portion of said media and said image receiving means, said diaphragm having a movable aperture for moving in concert with said light directing means so as to rapidly scan the sequentially illuminated portions of said article, the remainder of said diaphragm screening out glare and means for moving said light directing means and said diaphragm aperture in synchronization.

DESCRIPTION

The invention will become more apparent from the following detailed specification and drawings in which:

FIG. 1 is a sectional elevation view, partly in schematic, of a glare-reducing scanner embodying the present invention;

FIG. 2 is an elevation view of a diaphragm of the scanner of FIG. 1 taken on line 2—2 looking in the direction of the arrows;

FIG. 3 is an elevation view, partly in schematic, of an illumination means component of the present invention;

FIG. 4 is an elevation view of a part of the illumination means component of FIG. 3 taken on lines 4—4 looking in the direction of the arrows;

FIG. 5 is a sectional elevation view, partly in schematic, of another illumination means component of the present invention;

FIG. 6 is a sectional elevation view, partly in schematic, of yet another illumination means component of the present invention;

FIG. 7 is an elevation view of a diaphragm of the illumination component means of FIG. 6 taken along lines 7—7, looking in the direction of the arrows;

FIG. 8 is an elevation view of an alternate diaphragm of the illumination component means of FIG. 6;

FIGS. 9 to 15 illustrate various illumination patterns projected by the reduced glare scanner of the present invention;

FIGS. 16 to 18 are elevation views of various diaphragms employed in the scanner embodying the present invention;

FIG. 25 illustrates another embodiment of an illumination means component of the invention and FIG. 26 illustrates an enlarged cross-sectional schematic of a portion of the embodiment shown in FIG. 25.

Figure 19:
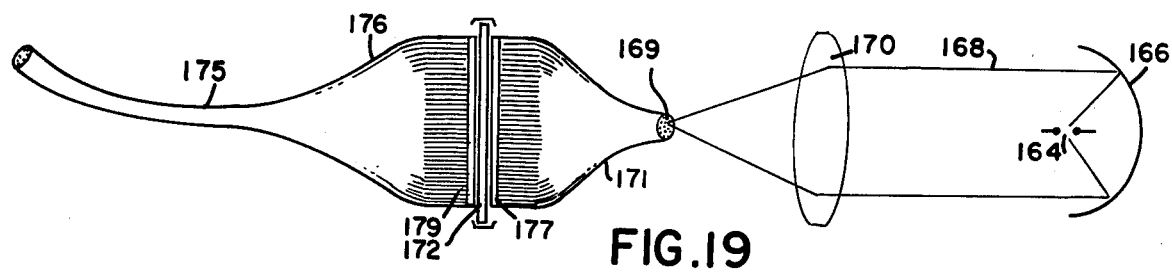
FIG. 19 is an elevation view, partly in schematic, of another illumination means component of the present invention.

Referring now to the drawings, the reduced glare scanner embodying the invention 10 has housing 12 having frontal lens 34 at the forward end thereof and a camera (film transport device) 11 at the rearward end thereof as shown in FIG. 1, and a plurality of lenses in-between as described below. Thus, at the forward end of the housing 12 is mounted objective lens cone 25 which contains foremost, as the first lens means, lens 34, preferably a contact lens and objective lens means 26 therebehind as shown in FIG. 1. The contact lens 34 is positioned in close proximity or in contact with the cornea of the eye to be observed. The fundus 27 of the eye 28 is illuminated by optic fiber bundle 30 which spreads into fibers mounted around the peripheral portion of the lens 34, which fibers together project a beam which illuminates a wide field of the fundus, also shown in FIG. 1. Further discussion of the illumination system follows below:

Behind the objective lens means 26 is collimating lens means 24 followed by focus tubes 14 and 16 which are axially moveable mounted within the housing 12 as shown in FIG. 1. The focus tube 14 has mounted at the forward end thereof, decollimating lens means 22, spaced from adjustable aperture diaphragm 20, which is mounted at the rear end of such tube as shown in FIG. 1. The focus tube 14 is moveable by knob 29. The focus tube 16 has objective lens means 18 mounted thereon and is moveable by knob 17 as shown in FIG. 1. The knobs 17 and 29 extend through narrow slots in the housing 12.

Behind the focus tube 16, within the housing 12 is positioned beam splitter 13 which directs a portion of the beam to portal A and finally the image receiving device, eg. film transport device or camera 11 as shown in FIG. 1.

In operation, the head of the patient is positioned on a chin rest (not shown) and the entire scanner 10 is brought into position proximate or in contact with the cornea of the patient's eye 28. The illuminating light is activated and travels through the optic fibers to project a beam which illuminates the fundus 27 of the eye 28 in a wide field. The beam 35, eg. from point 33 on the fundus 27 reflects back through the eye lens 36, through the pupil and the contact lens 34, through objective lens means 26 where the light beam converges to focal point 39 to form an intermediate image, thence diverges to collimating lens means 24, where the beam is rendered less divergent and directed rearwardly toward the focusing tube 14. The beam enters the focusing tube 14 through the decollimating lens means 22, which renders components of the beam less divergent and nearly parallel and directs such beam rearwardly through the diaphragm 20 (which reduces or blocks glare components of the beams), to the objective lens means 18, which converges the beam to a point or zone 37 on the image receiving means, e.g. film 15 of camera 11. In another example, points 41 and 45 on the fundus 27 reflect, respectively, principal rays 43 and 42 which are parallel between lens means 24 and 22 and pass through the respective lenses to points 49 and 51 on the camera film 11 as shown in FIG. 1. The focusing tubes 14 and 16 are moved within the housing 12 along the beam or beams until such beam is focused by the objective lens means 18 of the tube 14 on the image receiving means as seen by the observer at portal A thereof.

The focusing tubes 14 and 16 can be moved together or separately to obtain the desired focusing on the target area.

The illumination system 52 includes a series of scanning lamps 54 which are connected to power source 56 and which can be activated in sequence by switch 58. Variable resistor 60 controls the intensity of the activated lamp.

In focusing the system, the lamps 54 are turned on at reduced intensity and the light beam 62 is directed through lens 64 where it is focused on the fiber bundle 66 and transmitted to the frontal lens 34 and thence into the eye 28 to illuminate the fundus 27. The respective lenses 22 and 18 are moved within the housing 12 until the apparatus is focused on the fundus 27 as seen by the observer of portal A. At this point, appreciable glare is present in the received image due to reflections and diffusions in the eye lens 36, the frontal lens 34, and the interfaces of the cornea, and the objective lens 26 To significantly reduce this glare, the scanning means of the invention is introduced.

Thus, scanning diaphragm 68, a disc 70 having fins 72 and aperture 74, is positioned in air bearing channel 76 through housing 12 as shown in FIGS. 1 and 2. At this point, the intensity of the lamps 54 can be increased as desired by adjusting variable resistor 60. The disc 70 is rotated by a jet of air charged into the channel 76 at port 78 and vented at exit port 80. The rotating aperture 74 of the diaphragm sequentially scans the fundus 27 while the rest of the disc 70 blocks out reflected light from the fundus 27 and lenses 36, 26 and 24, reducing the glare in the received image.

To further reduce glare and as a further part of the scanning means, the lamps 54 and thus the ends in the fiber bundle 66 are sequentially illuminated and doused by rotating switch 58, such that successive portions of the fundus 27, are illuminated and doused. The scanning lamps 54 are synchronized with the RPM of the rotating scanning diaphragm 68 so that only that portion of the fundus 27 visible through the diaphragm aperture 74 at any instant is illuminated, further reducing reflected glare, haze and interference of the received image. The scanning diaphragm 68 and scanning lamps 54 are cycled at high RPM to provide a continuous appearing image to eye or camera.

In another embodiment of the invention, single lamp 82 having reflector 84 is activated at low intensity and a light beamed through focusing lens 86 toward fiber bundle 88 as shown in FIG. 3. The fiber bundle connects to a fundus observing apparatus, e.g. scanner 10 shown in FIG. 1. Again, the scanner lens system is focused on the fundus 27 in the low intensity light. The scanning prism 90 is positioned in the beam being transmitted to the fiber bundle 88 as shown in FIGS. 3 and 4. The prism 90 is pivotable, so as to direct the beam in sequence at successive optical fibers in the bundle 88 so as to sequentially illuminate successive portions of the fundus 27. The scanning prism 90 is synchronized with the RPM of the rotating, scanning diaphragm, e.g. diaphragm 68 of FIG. 1 above, the lamp intensity is increased as desired, and the received image is observed and/or photographed with the glare thereof significantly reduced.

In another embodiment of the invention, lamp 92 having reflector 94 is activated at low intensity to project a beam 95 through focusing lenses 96 and 98 to fiber bundle 100, as shown in FIG. 5. The fiber bundle connects to a fundus observing apparatus, e.g. scanner 10 shown in FIG. 1. Again, the scanner lens system is focused on the fundus in the low intensity light. The transmittal scanning diaphragm 107 is positioned in the beam 95 as shown in FIG. 5. The diaphragm 101 can be rotationally mounted on air bearings and be constructed like scanning diaphragm 68 shown in FIG. 2. Alternatively, a diaphragm 103 having pattern activator 107 can be mounted stationary and have an electronically defined moveable aperture thereon as illustrated in FIG. 16. In either case, after increasing the lamp intensity as desired, the diaphragm 101 (103) cycles so as to direct the beam in sequence at successive optical fibers so as to sequentially illuminate successive portions of the fundus, as above stated. Again, the transmittal scanning diaphragm 101 (103) is synchronized with the RPM of the scanning diaphragm, e.g. diaphragm 68 of FIG. 1 above and the glare or haze interference in the received image is significantly reduced.

In another embodiment of the invention, lamp 102, having reflector 104 is activated at low intensity to project a beam 105 through lenses 106 and 108 to elongated fiber bundle 110 as shown in FIG. 6. Again, the fiber bundle connects to a fundus observing apparatus similar to scanner 10, shown in FIG. 1, and the lens system thereof is focused. The reciprocal diaphragm 112, shown in FIGS. 6 and 7, is positioned in the beam 105 as shown in FIG. 6 and reciprocated in its track 113 across the beam 105 so as to block light from one side of the fibers and then the other and so to block light from one side of the fundus and then the other, e.g. fundus 27 of FIG. 1.

In another embodiment, reciprocal slotted diaphragm 114 having aperture 116 can replace diaphragm 112 in the illumination system of FIG. 6 so that in operation a slot of light scans the fibers and thus the fundus, e.g. fundus 27 of FIG. 1.

When either reciprocating diaphragm 112 or 114 is employed as described above, it is recommended that rotatable scanning diaphragm 68 in the scanner of FIG. 1 be replaced with a reciprocable scanning diaphragm which matches diaphragm 112 or 114 respectively. Again, the matching diaphragms are synchronized.

Whichever diaphragm is employed, the frequency thereof (including RPM), is high enough to present a clear continuous image of the fundus with a field of view of 80° to 150° and usually 100° or more to the observer or camera, e.g. as illustrated by 100° fundus field 115 shown in FIG. 15. Some of the patterns generated by the respective scanning diaphragm, were the frequency of their cycles slowed sufficiently, would appear as illustrated in the drawing. Thus, the projected pattern of diaphragm 68 of FIGS. 1 and 2, is shown as illuminated spots 118 on 100° field of view (of fundus) 120 rotating in the direction indicated by the arrow 122, as shown in FIG. 9.

The projected pattern of diaphragm 68 of FIGS. 1 and 2 can also appear as illuminated sector 124 on 100° fundus field 126, rotated in the direction indicated by arrow 128, as shown in FIG. 10.

The projected pattern of scanning prism 90 of FIG. 3 and 4 can also appear as illuminated spots 118 of fundus field 120 in FIG. 9, or a spiral (or other pattern) moving spot 130 on 100° fundus field 132 rotated in the direction indicated by the arrow 134 as shown in FIG. 11.

The projected pattern of scanning prism 90 of FIGS. 3 and 4 can also appear as concentric ring patterns, 136, 138 and 140 in 100° fundus field 142 shown in FIG. 12. This is accomplished by aiming the prism at selected groups of fibers which define the above rings in sequence.

The projected pattern of scanning reciprocal diaphragm 112, is illustrated as reciprocable shadow 144 on 100° fundus field 146, shown in FIG. 13. Similarly, the projected pattern of reciprocal scanning diaphragm 114 having aperture 116 is illustrated as reciprocal slot of light 48 on 100° fundus field 150 shown in FIG. 14.

In another embodiment, quarter sections of the fundus 152 can be sequentially scanned by U-shaped diaphragms 154 and 156 positioned at right angles to one another which reciprocate in turn, as indicated by the respective arrows, as shown in FIG. 17. The fundus 152 is illuminated in a corresponding pattern.

In another embodiment diaphragm 158, having matching ring shaped window 160 and circular window 162, can reciprocate to alternately scan the respective portions of the fundus (not shown) as shown in FIG. 18. The fundus is illuminated in a corresponding pattern.

All of the above patterns and others can be also accomplished with the use of electronically activated diaphragms in the scanner and positioned in the illuminating system which admit and exclude light in any desired pattern and cyclical rate, including those patterns illustrated in FIGS. 9 to 15, which patterns are not visible to the eye or camera at the higher frequencies employed. For example diaphragm 103 having power source 107 is shown in FIG. 16.

Figure 20:
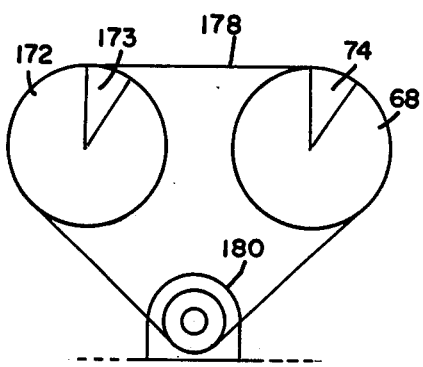
FIG. 20 is an elevation view of the illumination means component of FIG. 19 linked to a synchronized observation diaphragm.

A further illumination system embodying the invention, where a pair of belt-driven diaphragms rotate in concert is shown in FIGS. 19 and 20, wherein lamp 164 backed by reflector 166 is activated to project a beam 168 through focusing lens 170 to fiber bundle 169 having fibers 171. The fibers 171 are spread to terminate on support ring 177 proximate the periphery of diaphragm 172, the fibers 171 being in spaced matching registration with a second spread array of fibers 176 on support ring 179 on the reverse side of diaphragm 172, the fibers 176 converging to a fiber bundle 175 which leads to, for example, frontal lens 34 (shown in FIG. 1) as shown in FIG. 19. Light beams project across the gap between corresponding fibers 171 and 176 through the aperture 173 in diaphragm 172, shown in FIGS. 19 and 20. Illumination diaphragm 172 having aperture 173, is driven in phase (and in sync) with viewing diaphragm 68 having aperture 74 (shown in FIGS. 1 and 2) by endless belt 178 which is driven, in turn, by motor 180 shown in FIG. 20.

Figure 22:
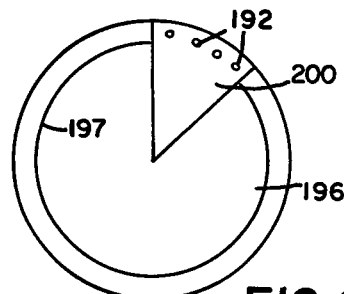
FIG. 22 is an elevation view of a diaphragm of the scanner of FIG. 21 taken on line 23—23 looking in the direction of the arrows.
Figure 21:
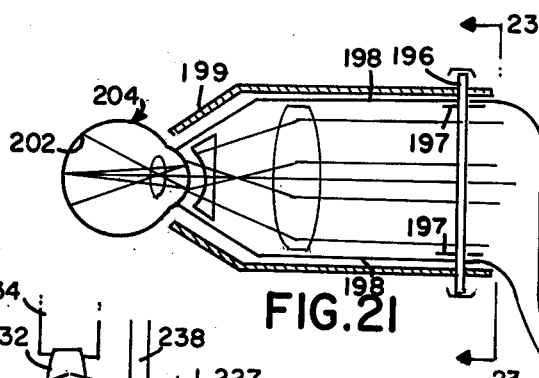
FIG. 21 is a sectional elevation view, partly in schematic, of another glare reducing scanner embodying the present invention.
Figure 24:
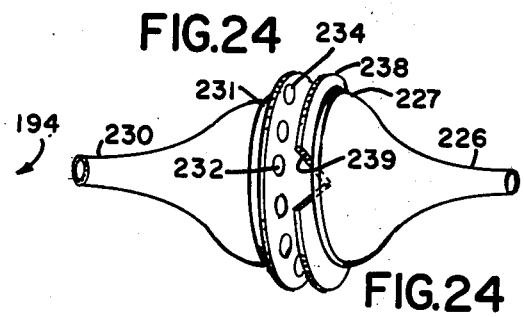

A preferred embodiment of the invention, where one diaphragm serves for two, is illustrated in FIG. 21, wherein lamp 182 backed by reflector 184, projects a beam 186 through focusing lens 188 to fiber bundle 190 having fibers 192. The fibers 192 extend to the reduced glare scanner of the invention 194 of FIG. 21, which scanner is constructed like the scanner 10 of FIG. 1 except for the illumination and diaphragm systems as discussed below. The fibers 192, upon entering the scanner 194, then fan out around the periphery of the dual diaphragm 196 and terminate proximate thereto or behind glare shield 197, illustrated in FIG. 21. On the reverse side of the diaphragm 196 also behind glare shield 197 is a second spread array of fibers 198 around the periphery thereof in spaced matching registration with the respective fibers 192 as shown in FIGS. 21 and 22. The fibers 198 extend from the dual diaphragm 196 forward within the scanner and converge to terminate in a mounting around the peripheral portion of the frontal lens 199 as shown in FIG. 21. The light beams project across the gap between corresponding fiber 192 and 198 through the aperture 200 in the diaphragm 196. The light is then projected through the fibers 198, through the contact lens 199 and into the fundus 202 of the eye 204 where it reflects back through the respective lenses of the eye and scanner 194 as discussed with respect to FIG. 2 and back through the aperture 200 within the glare shield 197 to the desired lens system or image receiving means eg for observation in photography. The rotation of the diaphragm 196 and thus the aperture 200 thus provides for sequential illumination and observation of the same portion of the fundus 202 of the eye 204 at the same time while the diaphragm blocks excess glare. Accordingly, illumination and observation of the eye is automatically synchronized and reduced glare scanning thereof for high clarity observation and photography of the eye is achieved.

Figure 23:
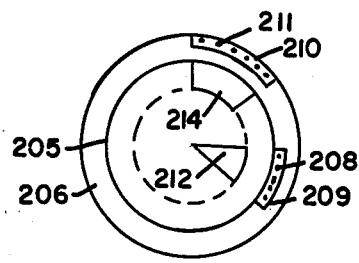
FIG. 23 is an elevation view of an alternate diaphragm for the scanner of FIG. 21.
Figure 24:
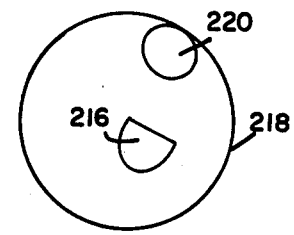
FIG. 24 illustrates another illumination pattern projected by the scanner embodying the invention.

The dual diaphragm of the invention can have various shaped apertures, singular or plural, according to the pattern of scanning desired. For example, the diaphragm 206 has illumination apertures 208 and 210, outside of glare shield 205, and two associated observation apertures 212 and 214 as shown in FIG. 23. As the diaphragm rotates, aperture 208 scans inner row of fibers 209 which illuminate (rotating) center spot 206 on the fundus 218 as observed through aperture 212 and aperture 210 scans outer row of fibers 211 which illuminate (rotating) outer spot 20 as observed through aperture 214 as shown in FIGS. 23 and 24.

For the scanner 194, various other diaphragms can be employed including those illustrated in FIGS. 2 through 8 and including rotating and oscillating diaphragms and electronically activated diaphragms.

Thus, the scanning system of the invention provides for wide angle illumination, focusing observation and photography of objects including the fundus of the eye through transparent, reflective and diffusive media (including lenses) while significantly reducing haze and glare interference and obtaining previously unavailable quality of images and pictures of high clarity and definition.

Of course the scanning system of the invention can be employed with other lens systems than that shown in FIG. 1. The lens system was chosen only as an example and the scanning means of the present invention can be employed with virtually any lens system employed for observing (eg. an ophthalmoscope) and/or photographing the interior of the eye. Of course, the lens system illustrated in FIG. 1 has the advantage of having, in addition to, the observation diaphragm 68, an additional diaphragm 20, which further screens out peripheral glare in accordance with the size of the aperture thereof. However, this second diaphragm 20 is not essential to the functioning of the scanning diaphragm disclosed in the present invention.

The observation diaphragm can be located at the intermediate image 39 but is preferably located a distance therefrom either in front of the lens 24 or behind at a short distance (as shown in FIG. 1) or a greater distance, as indicated in FIG. 21 or even further back (past lens 22) if desired. Preferably the observation diaphragm is located in the parallel portion of the reflected beam, eg. between lenses 24 and 22, shown in FIG. 1.

The scanning diaphragm in the lens system, eg. diaphragm 68, can be employed with steady, uninterrupted illumination, for example to the fundus of the eye and will alone screen out considerable glare. Preferably, however, the scanning diaphragm, such as diaphragm 68, is employed in conjunction with selective illumination scanning means eg. sequential lamps 54 of FIG. 1, rotatable prism 90 of FIG. 3, a matching illumination diaphragm and the like.

The cyclic speed at which scanning must take place to present a continuous image to observer's eye or the camera, is as follows. For continuous observation of the fundus, the scanning diaphragm should cycle at about 1 revolution per 1/10th second, or more. For a camera having a shutter speed of 1/60th second, the scanning diaphragm should cycle at 1 revolution per 1/60th of a second or more. Higher speeds than those discussed above will of course result in better uniformity and will be needed for faster camera settings.

The above speeds hold true whether the lens system scanning diaphragm and illumination system scanning means are reciprocating rotating, either smoothly or intermittently (stop-go rotation), tracing a spiral, linear or other path. In any case, a high revolution or cycles per second, should be maintained for observation and or photography purposes.

At such high cyclic speeds, e.g. 40,000 RPM, it is highly difficult to synchronize, for example a rotating scanning diaphragm, e.g. diaphragm 68 of FIG. 1, with another mechanical cyclical scanning means in the illumination system, such as prism 90 in FIG. 3 or rotating diaphragm 101 of FIG. 5. Accordingly, it is recommended that where one scanning diaphragm is mechanically cycled, the matching scanning means, e.g. in the illumination system, should be one that is electrically or electronically cycled in synchronization with the mechanically cycled diaphragm since the latter can more readily be synchronized with the former. Of course, when both the lens system scanning diaphragm and the illumination scanning means are both electronic, then synchronization thereof is more readily attained and maintained. Alternatively two diaphragms can be mechanically driven in sync by a common endless belt as discussed above.

A preferred scanning system according to the present invention is illustrated in FIGS. 1 and 2, wherein the scanning diaphragm 68 mechanically rotates on air bearings and the scanning means in the illumination system is an electrically cycled series of lamps, which systems can be readily syncronized.

A more preferred scanning system according to the present invention is illustrated in FIGS. 21 and 22 where the dual purpose diaphragm is employed in place of two and no synchronization is necessary.

Although in the systems described herein, the illumination beams are separate from the viewing of camera beams because this is the preferred system, other lighting systems may be employed within the scope of the present invention. Thus, illuminating systems which beam light through the viewing or observation lens system or any transparent but reflective medium are included within the scope of the present invention.

Although various lamps can be employed for illuminating at low intensity and at high intensity and for bright or flash lighting of the fundus of the eye or other objects, the lamp for bright lighting of the fundus, is preferably a Xenon arc lamp, with a concave, (including ellipsoid and paraboloid) reflector, preferably a paraboloid reflector and preferably with the electrodes of the arc lamp positioned so that the axes thereof coincide with the axis of the reflector. These lamps can be employed with dimming means to focus in the system, after which the light can be brightened or dimmed and bright lamps can be substituted as needed.

Although various illumination and observation scanning means have been disclosed herein, various other means which selectively or sequentially scan portions of an article including the fundus of the eye are included within the scope of the present invention.

In addition to single axis alighment of the lens components of the receiver illustrated in FIG. 1, various other multi-axis lens alignment embodiments be provided within the scope of the scanner of the present invention. For an illustration of multi-axes lens alighment, see my co-pending patent application described above.

Between the objective lens means of the focusing lens assembly and the image receiving means, can be positioned a beam splitter, which, as discussed above, directs a portion of the beam to an image receiving means, e.g. a camera, and directs another portion of said beam to another image receiving means, e.g. a viewing portal for an observer, a TV or other camera, a scope and the like. The beam splitter can be a prism and a flat piece of glass of equivalent index of refraction or a cube beam splitter. The beam splitter can be dispensed with if desired. A reflex camera, where employed, provides a viewing portal through the camera lenses.

Other objects or articles besides the interior of the eye can be focused upon and observed through the scanner of the present invention. Objects, where removing glare for a clear picture is desirable, can be readily viewed and photographed through the apparatus of the present invention, e.g. the interior of locks, insects and miniature electronic equipment, as well as larger objects where it is necessary to observe through transparent reflective and diffusive media. (glass lenses, etc.) Preferably, the scanner embodying the present invention is highly suited for wide-angle illumination, observation and photographing of the fundus of the eye with sharply focused, glare-free clarity.

The image receiving means at the end of the image receiver can include the observation eye, film, TV, motion and still cameras and scopes and measuring devices, e.g. reflectometer or a combination thereof.

Figure 26:
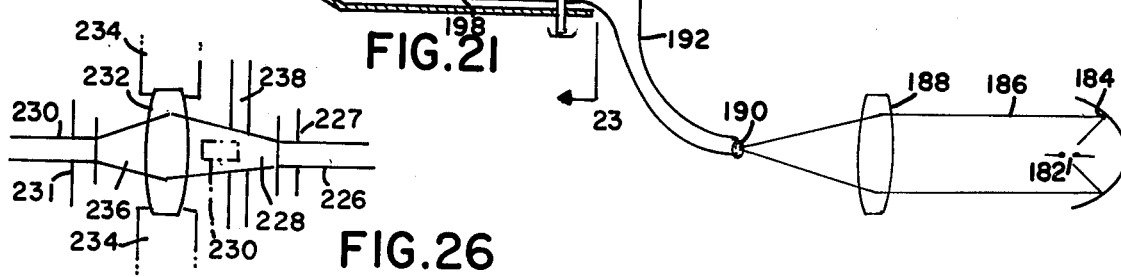

In the embodiments of the present invention illustrated in FIGS. 19 and 21, the light projected between spaced opposed fibers (or bundles of fibers) can be more fully utilized by placing a focusing lens in the gap therebetween. Thus optical fiber 226 bonded to support ring 227 emits light in a divergent beam 228, the outer portions of which by-pass closely spaced opposed optical fiber 230 (in phantom) so that considerable light is lost therebetween, as shown in FIG. 26. To correct this loss, optical fiber 230 mounted on support ring 231 is moved back from optical fiber 226 and lens 232, mounted on support ring 234, inserted therebetween to convert diverging beam 238 to convergent beam 236, which can be focused (by suitably positioning lens 232) to enter optical fiber 230, (or bundle of fibers) which may be of larger, the same or even smaller diameter than optical fiber 226, with little or virtually no light lost as shown in FIG. 26. Diaphragm 238 is also mounted in the gap adjacent lens support ring 234, also as shown in FIG. 26.

Accordingly the illumination system illustrated in FIG. 19 can achieve greater illumination efficiency by employing between spaced opposed optical fibers 226 and 230 a multi-lens ring 234 and a rotatable diaphragm 238 having an aperture 239 therein as shown in FIGS. 25 and 26. The multi-lens ring 234, has mounted therein, a plurality of lenses 232, each lens being situated between a pair of spaced opposed fibers 226 and 230 as shown in FIGS. 25 and 26. The multi-lens ring 234 is shiftable sidewise to achieve the proper focus of the beams 236 on the fibers 230 and thereafter is secured in place.

The multi-lens ring 234 of the invention can be employed on either side of the diaphragm 238 but is preferably positioned on the remote side thereof as illustrated in FIG. 25. While preferred, the multi-lens ring 234, can, where desired, be replaced by a single large lens of suitable focal length, such as lens 64 shown in FIG. 1 herein. The optical fibers 226 and 230 can, of course be replaced by individual optic fiber bundles, where desired. Further the multi-lenses can be mounted on a support shaped like a disc, square or other shape as desired, where, as in the fiber array of FIG. 19, there is no need of an aperture or window through the center thereof. Finally, the multi-lens ring of the invention or a single large lens of suitable focal length, can be employed in the fibers gap adjacent the diaphragm 196 in the apparatus shown in FIG. 21 or in other interrupted fiber systems employed in the reduced glare scanner embodying the invention.

What is claimed is:

1. Apparatus for reduced glare observation of an article through transparent, partially reflective and diffusive media wherein said media is located proximate said article and between said apparatus and said article, which apparatus comprises, an image receiving means; illumination means which directs an unfocused beam of light onto said article; light directing means to direct said light beam to rapidly and repeatedly illuminate successive portions of said article, which light is reflected from said article through said media to said image receiving means; an observation diaphragm positioned between said media and said image receiving means in the path of the above reflected light removed from and proximate to a focused image zone of said article, said diaphragm having a moveable aperture for moving in concert with said light directing means so as to rapidly scan the sequentially illuminated portions of said article, the remainder of said diaphragm screening out glare and means for moving said light directing means and said diaphragm aperture in synchronization.

2. The apparatus of claim 1 wherein said illumination means is at least one lamp and said light directing means is a rotatable sector diaphragm mounted between said lamp and said article and means to rotate said diaphragm to illuminate in sequence portions of said article.

3. The apparatus of claim 1 wherein said illumination means is a lamp and said light directing means is a moveable prism mounted between said lamp and said article, which prism directs light at a portion of said article and means for moving said prism to illuminate in sequence portions of said article.

4. The apparatus of claim 1 wherein said illumination means is a plurality of lamps which are selectively illuminated and darkened to sequentially illuminate portions of said article.

5. The apparatus of claim 1 wherein said light directing means is an illuminating diaphragm positioned in the path of light beamed to said article and mounted to move in concert with said observation diaphragm.

6. The apparatus of claim 5 wherein said diaphragms are rotated by an endless belt.

7. The apparatus of claim 1 wherein positioned between said light directing means and said article is a plurality of optical fibers which receive the light from said light directing means and transmit same to the article illuminated.

8. The apparatus of claim 7 wherein said article is the fundus of the eye, said media includes the cornea, the aqueous humor, the lens and the vitreous humor of said eye and said fibers terminate at and are mounted around a light receiving portal for said image receiving means and said fibers beam light onto the fundus of the eye.

9. The apparatus of claim 2 wherein the illumination means beams light to an optical fiber bundle, the fibers of which diverge and terminate in a first spread pattern, a second spread pattern of fibers spaced from said first spread pattern with the opposed fibers in registration therewith, said second pattern of fibers converging to a second fiber bundle which transmits light to said article and an illuminating diaphragm positioned between said first and second fiber patterns and mounted to move in concert with said observation diaphragm.

10. The apparatus of claim 1 wherein said light directing means illuminates in sequence part of said article in a cycle at the rate of at least 1 cycle per 1 second.

11. The apparatus of claim 1 wherein said light directing means illuminates in sequence portions of said article at the rate of a least 1 cycle per 1/60th second.

12. The apparatus of claim 1 wherein said observation diaphragm means has an aperture therein and means for rotating said diaphragm on an axis normal thereto to rotate said aperture.

13. The apparatus of claim 9 wherein said aperture is a wedge shaped sector with apex proximate the center of said diaphragm.

14. The apparatus of claim 1 wherein said diaphragm aperture is reciprocated before said media so as to scan the illuminated portion of said article.

15. The apparatus of claim 1 wherein said diaphragm is rotated on an air bearing.

16. The apparatus of claim 1 wherein said diaphragm is rotated intermittently.

17. The apparatus of claim 1 wherein said diaphragm has an electronically created aperture which is activated to scan said article.

18. The apparatus of claim 1 wherein said diaphragm is a dual purpose diaphragm having at least one light transmitting aperture near the periphery thereof and at least one observation aperture within said periphery, said light directing means directs light through said light transmitting aperture to said article, said light being reflected through at least a portion of said media and through said observation aperture to said image receiving means and means for moving said diaphragm and thus said apertures so as to rapidly scan sequentially illuminated portions of said article.

19. The apparatus of claim 18 wherein the ilumination means beams light to an optical fiber bundle, the fibers of which diverge and terminate in a first spread pattern arrayed around the periphery of said diaphragm in close spaced proximity therewith, a like second spread pattern of fibers arrayed proximate the reverse side of said diaphragm with the opposed fibers in registration with the first pattern of fibers, said second pattern of fibers extending out of the path of said reflected light forward from said diaphragm to said article to illuminate the same.

20. The apparatus of claim 1 wherein said image receiving means is an observation window.

21. The apparatus of claim 1 wherein said image receiving means is a camera.

22. The apparatus of claim 9 wherein a multi-lens support is positioned between said first and second fiber patterns and adjacent said illuminating diaphragm, said support having mounted therein a plurality of lenses, each lens being mounted between a pair of spaced opposed fibers to focus the light rays transmitted therebetween.

23. The apparatus of claim 9 wherein a single lens of sufficient size is interposed between said first and second fiber patterns to focus the light rays transmitted between opposed fibers.

24. The apparatus of claim 19 wherein a multi-lens support is positioned between said first and second fiber patterns and adjacent said illuminating diaphragm, said support having mounted therein a plurality of lenses, each lens being mounted between a pair of spaced opposed fibers to focus the light rays transmitted therebetween.

25. The apparatus of claim 19 wherein each fiber is replaced by a fiber bundle.

26. A method for reduced glare observation of the fundus of an eye through transparent, reflective and diffusive media comprising, directing scanning light to rapidly illuminate successive portions of said fundus repeatedly, admitting the reflected light from the then illuminated portion of said fundus to an image receptor while blocking substantially all the glare and reflected and diffused light from the rest of the scanned portion of said fundus by moving a diaphragm across the path of said reflected light, removed from and proximate to a focused image zone of said article so as to obtain a clear image of substantially all the scanned portion of said fundus by rapid observation scanning of the sequentially illuminated portions thereof.

27. The method of claim 26 wherein said observation scanning occurs through the aperture of a diaphragm and said aperture is moved across the path of said reflected light in concert with said scanning light.

28. The method of claim 26 wherein said scanning light is transmitted to said fundus by way of fiber optics.

29. The method of claim 26 wherein said article is the fundus of an eye.

30. The method of claim 26 wherein said image receptor is the human eye.

31. The method of claim 26 wherein said image receptor is a camera including a film camera and a television camera.

* * * * *